United States Patent [19]
Müller et al.

[11] Patent Number: 5,132,335
[45] Date of Patent: Jul. 21, 1992

[54] ACRYLIC AND METHACRYLIC ESTERS OF SUBSTITUTED 1,2-BIS(PHENOXY)-3,3,4,-4,5,5-HEXA-FLUORO-1-CYCLOPENTENES

[75] Inventors: Michael Müller, Bergisch Gladbach; Wolfgang Podszun, Cologne; Jens Winkel, Cologne; Michael Negele, Cologne, all of Fed. Rep. of Germany

[73] Assignee: Bayer Aktiengesellschaft, Leverkusen, Fed. Rep. of Germany

[21] Appl. No.: 653,397

[22] Filed: Feb. 11, 1991

[30] Foreign Application Priority Data

Feb. 20, 1990 [DE] Fed. Rep. of Germany ....... 4005231

[51] Int. Cl.$^5$ .................. A61C 5/10; C08C 69/52; C08F 18/20
[52] U.S. Cl. ........................ 522/96; 522/97; 522/98; 522/908; 523/116; 526/245; 526/246; 526/301; 526/320; 560/220; 560/221; 433/223; 433/228.1
[58] Field of Search ................ 560/220, 221; 522/96, 522/97, 98, 908; 526/245, 246

[56] References Cited

U.S. PATENT DOCUMENTS

| | | | |
|---|---|---|---|
| 3,923,740 | 12/1975 | Schmitt et al. | 560/221 |
| 4,117,240 | 9/1978 | Kline | 560/221 |
| 4,347,174 | 8/1982 | Nagase et al. | 522/908 |
| 4,616,073 | 10/1986 | Antonucci | 526/246 |
| 4,665,217 | 5/1987 | Reiners et al. | 522/181 |
| 4,752,338 | 6/1988 | Reiners et al. | 560/221 |
| 4,839,401 | 6/1989 | Waknine | 522/908 |
| 4,910,275 | 3/1990 | Yamazaki et al. | 526/245 |
| 4,985,473 | 1/1991 | Williams et al. | 522/97 |
| 4,990,633 | 2/1991 | Negele et al. | 560/15 |
| 5,008,436 | 4/1991 | Müller et al. | 560/220 |

*Primary Examiner*—Marion E. McCamish
*Assistant Examiner*—Susan Berman
*Attorney, Agent, or Firm*—Sprung, Horn, Kramer & Woods

[57] ABSTRACT

Acrylic and methacrylic esters of substituted 1,2-bis(-phenoxy)-3,3,4,4,5,5-hexafluoro-1-cyclopentenes of the formula

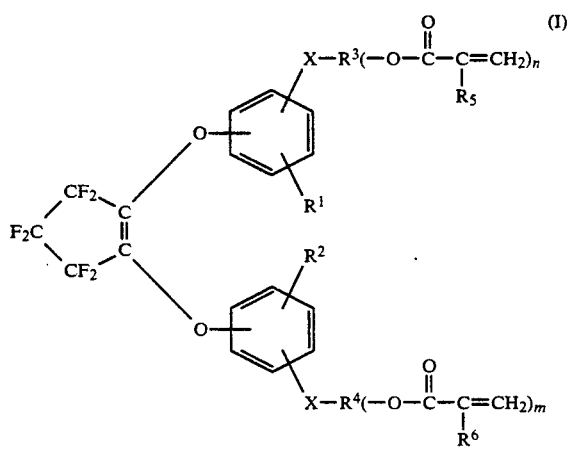

in which, in each case independently of one another,
$R^1$ and $R^2$ denote $C_1$-to $C_4$-alkyl, $C_1$- to $C_4$-halogenoalkyl or hydrogen,
$R^3$ and $R^4$ denote $(n+1)$- or $(m+1)$-valent, straight-chain or branched hydrocarbon radicals having 2 to 15 carbon atoms, which may optionally contain 1 to 3 oxygen bridges,
$R^5$ and $R^6$ denote hydrogen or methyl,
X represents

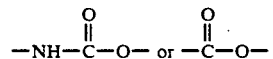

and
n and m denote integers from 1 to 5

The ester can be polymerized to form dental fillings, coatings and artificial teeth.

9 Claims, No Drawings

ACRYLIC AND METHACRYLIC ESTERS OF SUBSTITUTED 1,2-BIS(PHENOXY)-3,3,4,-4,5,5-HEXAFLUORO-1-CYCLOPENTENES

The invention relates to new acrylic acid and methacrylic acid esters of substituted 1,2-bis(phenoxy)-3,3,4,4,5,5-hexafluoro-1-cyclopentenes, their preparation and their use as monomers for application in the dental field.

In conventional dental filling materials, dental lacquers and special adhesives for dental applications, the organic matrix consists, inter alia, of 2,2-bis-[4,(3-,,-methacryloyl-2,,-hydroxypropoxy)phenyl]-propane (bis-GMA). The plastics prepared therefrom by polymerization are relatively strongly hydrophilic and undergo degradation as a result of combined chemical and physical stress in the mouth of the patient. Owing to their hydrophilic nature, these plastics absorb water and chemicals and bacteria found therein, which, for example, are formed in the digestive process in the mouth, in the moist oral medium. This leads over a relatively long period of time to a decrease in the hardness and resistance to abrasion of these materials and in addition promotes attack by plaque and thus the formation of secondary caries.

The use of fluorine-containing compounds is already known for the hydrophobization of dental materials. Fluorine-containing phenylcarbinol acrylates such as 1,1,1,3,3,3-hexafluoro-2-phenyl-2-acryloyloxy-propane are known from Org. Coat. Plast. Chem. 42 (1980) 204. Similarly synthesized (meth)acrylic acid esters, such as 1,3-bis-(2-(meth)acryloyloxy-1,1,1,3,3,3-hexafluoro-prop-2-yl)-5-perfluoroalkyl-benzene and its use in the dental field are described in U.S. Pat. No. 4,356,296. Owing to the trifluoromethyl groups, the carbinols are made acidic and the carbinol esters prepared therefrom are distinguished by reduced resistance to hydrolysis. As a result, their utilizability as dental monomers is restricted.

Furthermore, the use of 1,1,5-trihydro-octafluoropentyl methacrylate in dental filling materials is described in J. Dent. Res. 58 (1979) 1181 (U.S. Pat. No. 4,292,029). Monomers of this type give dental materials having a poor mechanical property level and are to be evaluated critically in their processing behavior and from toxicological considerations owing to their high vapor pressure. (Meth)acrylates containing trifluoromethyl groups according to EP 295,639 are formed by successive reaction of hexafluoro-2-propanol units with the carcinogenic epichlorohydrin, base and methacrylic acid, the resulting product containing strongly hydrophilic hydroxypropyl groups. In Polym. Mater. Sci. Eng. 59 (1988) 388, polyfluorinated methacrylates ("PFMA", U.S. Pat. No. 4,616,073) and urethane methacrylates ("PFUMA") are described which are formed from a polyfluorinated polyol in a polymer-analogous reaction. The completeness of the reaction of the OH functions of the polyol in this case has to be evaluated just as critically as the availability of the chemicals employed, such as 2-isocyanatoethyl methacrylate.

(Meth)acrylic acid esters having a central 1,2-diphenyl-1,1,2,2-tetrafluoroethane building block are additionally known from DE-OS (German Published Specification) 3,516,256 and DE-OS (German Published Specification) 3,516,257.

New (meth)acrylic acid esters of substituted 1,2-bis-(phenoxy)- 3,3,4,4,5,5-hexafluoro-1-cyclopentenes of the formula (I)

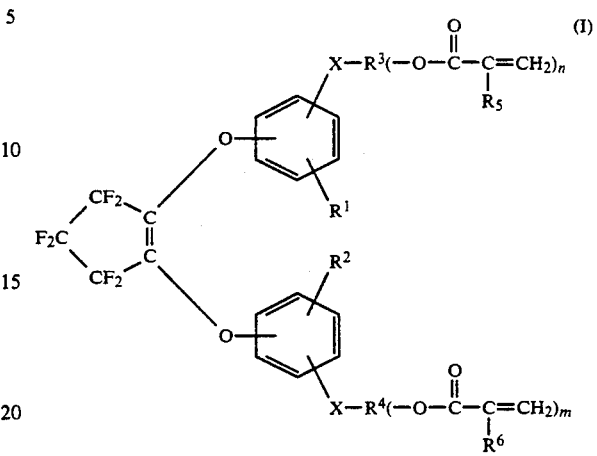

have now been found in which, in each case independently of one another, $R^1$ and $R^2$ denote $C_1$- to $C_4$-alkyl, $C_1$- to $C_4$-halogenoalkyl or hydrogen, $R^3$ and $R^4$ denote (n+1)- or (m+1)-valent, straight-chain or branched hydrocarbon radicals having 2 to 15 carbon atoms, which may optionally contain 1 to 3 oxygen bridges, $R^5$ and $R^6$ denote hydrogen or methyl, X represents

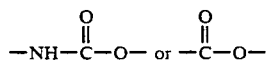

and n and m denote integers from 1 to 5.

In the context of the present invention, the substituents in general can have the following meanings $C_1$- to $C_4$-alkyl can denote a straight-chain or branched hydrocarbon radical having 1 to 4 carbon atoms. Examples which may be mentioned are the following alkyl radicals: methyl, ethyl, propyl, isopropyl, butyl and isobutyl. The methyl radical is preferred. Hydrogen is particularly preferred for the radicals $R^1$ and $R^2$. In the case of $C_1$- to $C_4$-halogenoalkyl radicals, these can be radicals having one or more identical or different halogen atoms. Suitable halogen atoms are fluorine, chlorine, bromine and/ or iodine, and fluorine, chlorine and/or bromine are preferred, in particular fluorine and/or chlorine. The halogen atom or atoms can be located in an internal position or terminal position A particularly preferred group of $C_1$- to $C_4$-halogenoalkyl radicals are the perfluoroalkyl radicals; the trifluoromethyl group is very particularly preferred. In the context of the substituents $R^3$ and $R^4$, the (n+1)- or (m+1)-valent hydrocarbon radicals can be straight-chain or branched and contain 2 to 15, preferably 2 to 10 and particularly preferably 2 to 5, carbon atoms. For $R^3$ and $R^4$, these hydrocarbon radicals may optionally also contain 1 to 3 oxygen bridges, preferably 1 or 2 oxygen bridges.

The valencies of the substituents are determined by n and m. n and m independently of one another represent integers from 1 to 5, preferably 1 and 2.

Examples of the substituents $R^3$ and $R^4$ which may be mentioned are the following radicals:

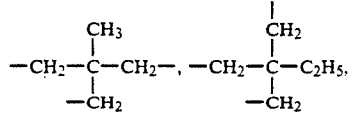

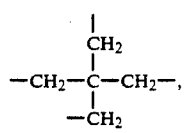

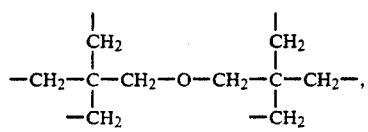

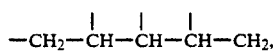

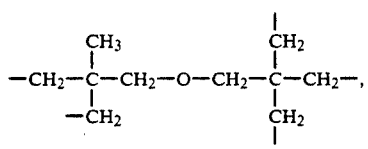

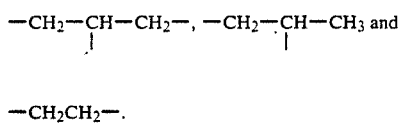

—CH$_2$CH$_2$—.

The radicals $R^5$ and $R^6$ represent hydrogen or methyl. In the context of the present invention, this is expressed in the designation (meth)acrylic acid esters, by which esters of acrylic or methacrylic acid are meant. Methyl is preferred for the radicals $R^5$ and $R^6$.

The new (meth)acrylic acid esters according to the invention are colorless, poorly volatile, low viscosity oils and yield transparent plastics after polymerization. In the context of the present invention, it is also preferred to add mixtures of different (meth)acrylic acid esters according to the invention. They can be used particularly well in sealing agents, adhesives and preferably dental materials, such as dental filling materials and coating agents. The materials thus obtained are distinguished by a surprisingly large resistivity to physical and chemical stress. To a particular extent, the mechanical properties are improved compared to customary materials employed for this purpose. The favorable surface properties and low water absorption of the polymers obtained using the new (meth)acrylic acid esters are particularly to be emphasized.

Preferred (meth)acrylic acid esters of substituted 1,2-bis(phenoxy)-3,3,4,4,5,5-hexafluoro-1-cyclopentenes are compounds of the formula (I)

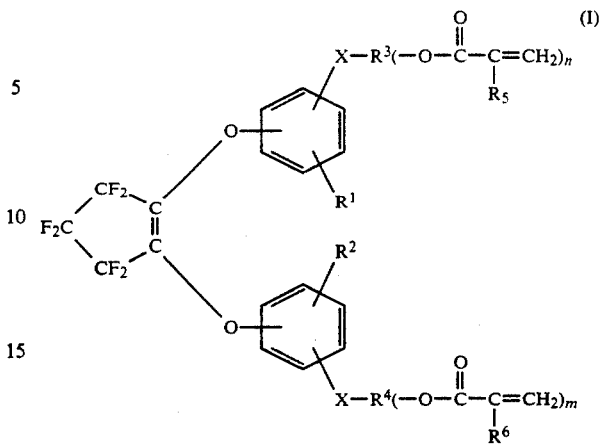

in which, in each case independently of one another,
$R^1$ and $R^2$ denote hydrogen or trifluoromethyl,
$R^3$ and $R^4$ denote (n+1)- or (m+1)-valent, straight-chain or branched hydrocarbon radicals having 2 to 15 carbon atoms,
$R^5$ and $R^6$ denote hydrogen or methyl,
X represents

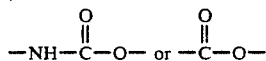

and
n and m denote 1 or 2.

Examples which may be mentioned are the following (meth)acrylic acid esters according to the invention, the symbol

being chosen for the 3,3,4,4,5,5-hexafluoro-1-cyclopentene ring.

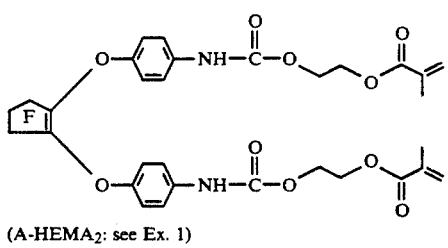

(A-HEMA$_2$: see Ex. 1)

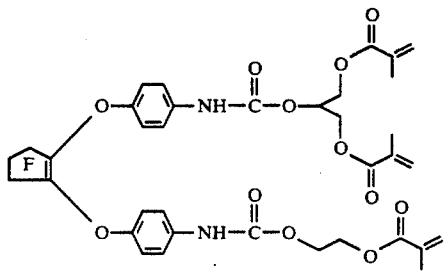

-continued
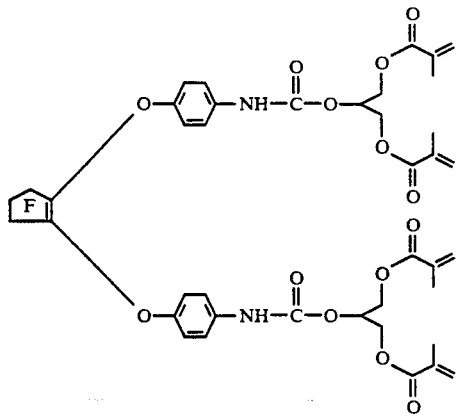
(A-GDMA₂: see Ex. 2)
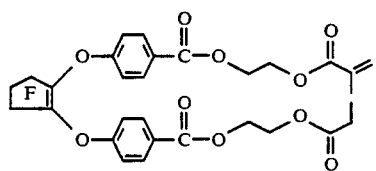
(B-HEMA₂: see Ex. 3)
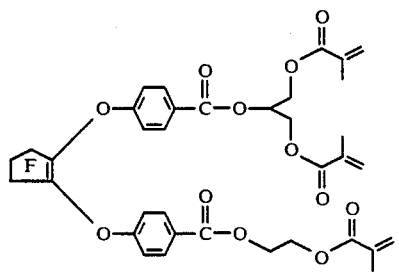
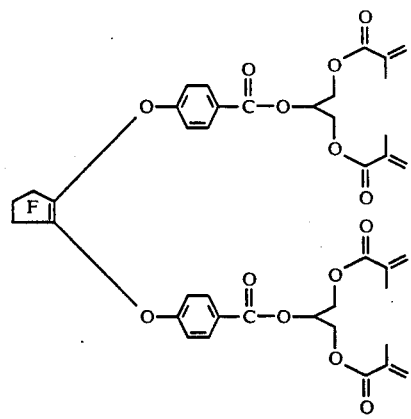
(B-GDMA₂: see Ex. 4)
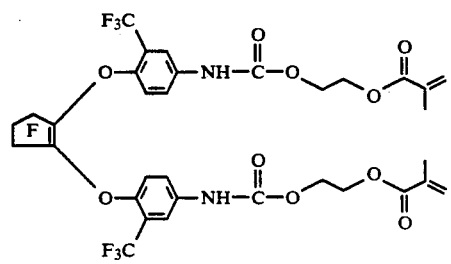
-continued
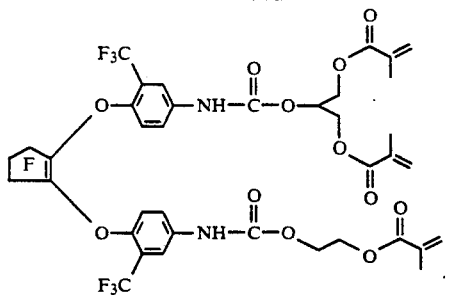
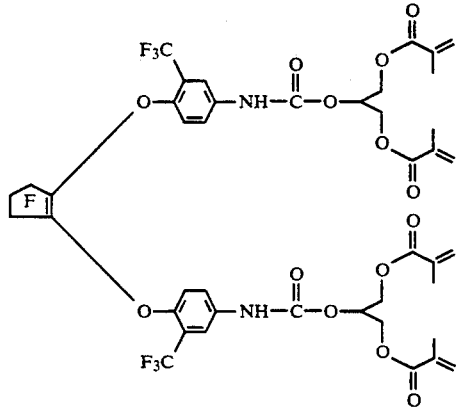
(C-GDMA₂: see Ex. 5)
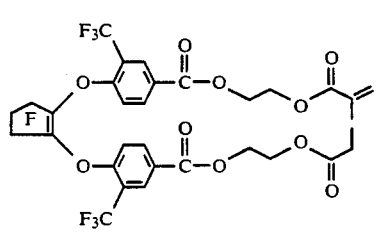
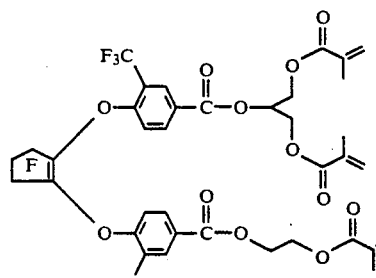
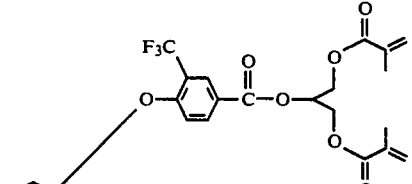
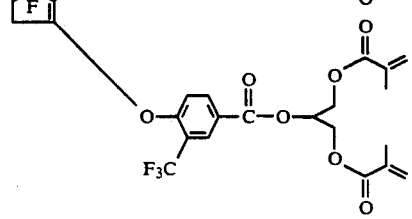

-continued
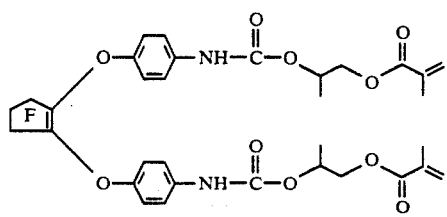
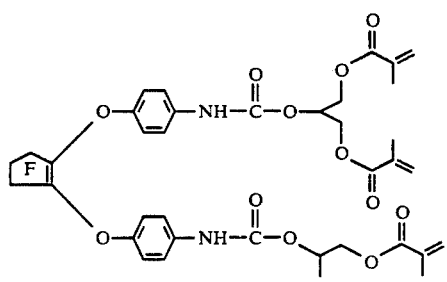
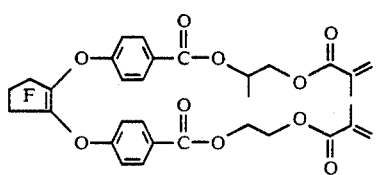
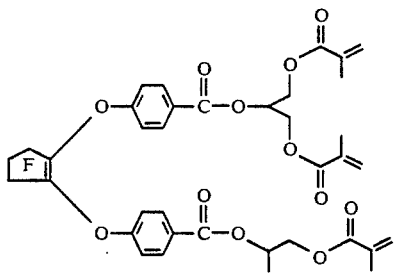
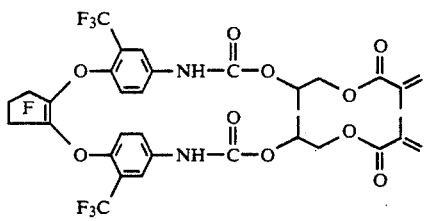
(C-HPMA₂: see Ex. 5)
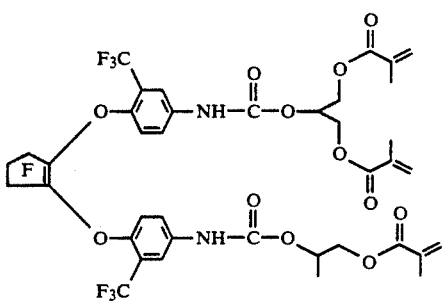
(C-GDMA-HPMA: see Ex. 5)
-continued
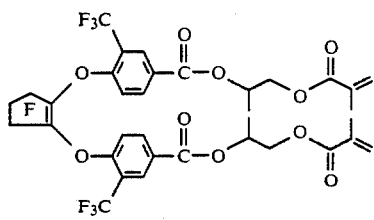
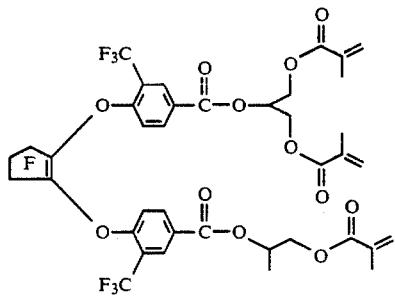
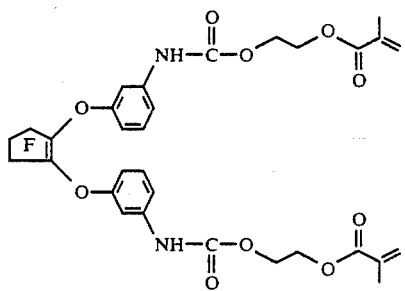
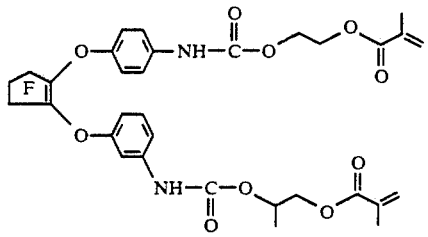
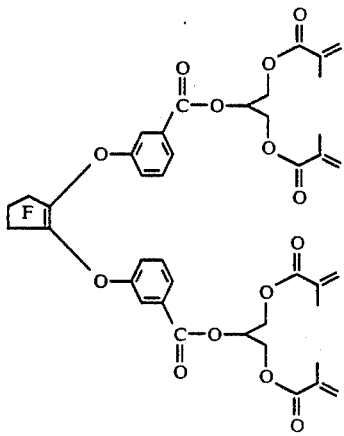
and -continued

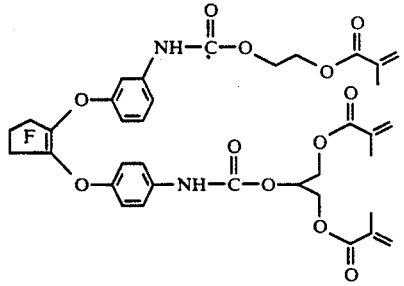

A process for the preparation of (meth)acrylic acid esters of the formula (I) has furthermore been found, which is characterized in that substituted 1,2-bis-(phenoxy)-3,3,4,4,5,5-hexafluoro-1-cyclopentenes of the formula

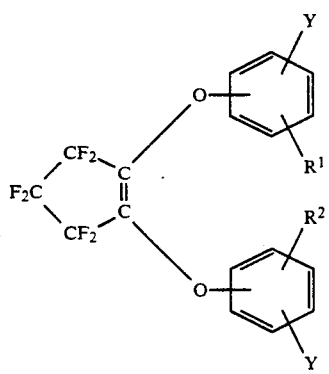 (II)

in which

R$^1$ and R$^3$ independently of one another denote

C$_1$- to C$_4$-alkyl,

C$_1$- to C$_4$-halogenoalkyl or hydrogen and

Y represents isocyanato (—NCO) or chlorocarbonyl (—COCl), are reacted with at least one OH-functional (meth)acrylic acid derivative of the formula

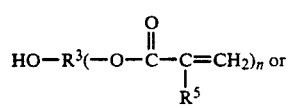 (III)

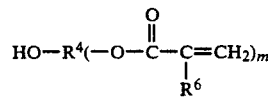 (IV)

in which, independently of one another,

R$^3$ and R$^4$ denote (n+1)- or (m+1)-valent, straight-chain or branched hydrocarbon radicals having 2 to 15 carbon atoms, which may optionally contain 1 to 3 oxygen bridges, R$^5$ and R$^6$ denote hydrogen or methyl and n and m denote integers from 1 to 5, in an inert solvent, in the temperature range between —40° and +100° C., optionally in the presence of a catalyst and/or a base and optionally in the presence of a polymerization inhibitor.

The preparation of the substituted 1,2-bis-(phenoxy)-3,3,4,4,5,5-hexafluoro-1-cyclopentene of the formula (II) required for the process according to the invention is known from DE-OS (German Published Specification) 3,817,626. Suitable compounds of the formula (II) which may be mentioned are:

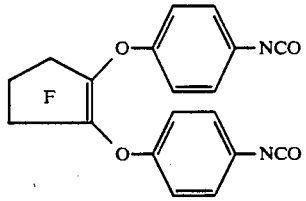

(A; see Ex. 1 and 2),

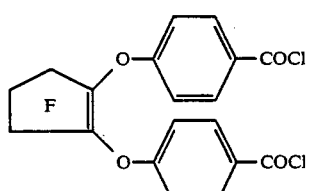

(B; see Ex. 3 and 4),

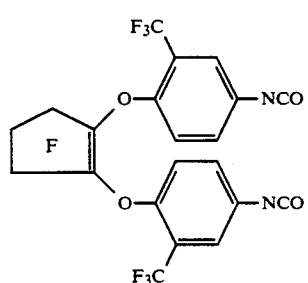

(C; see Ex. 5),

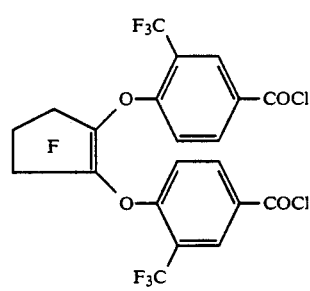

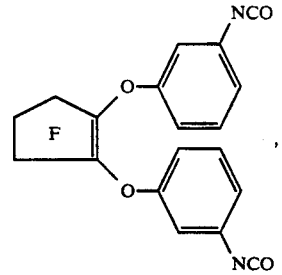

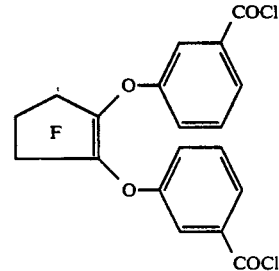

-continued

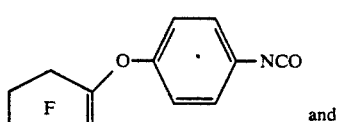
and
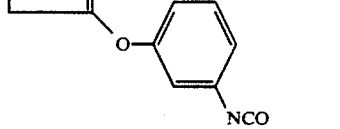

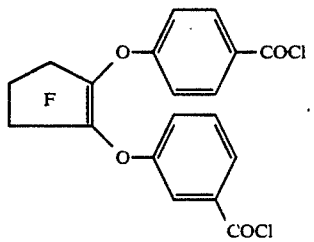

OH-functional (meth)acrylic acid derivatives of the formulae (III) and (IV) are available commercially or can be prepared in a known manner by partial esterification of the corresponding polyols HO—R³(OH)  or  HO—R⁴(OH)$_m$.

Suitable OH-functional (meth)acrylic acid derivatives which may be mentioned are: dodecanediol mono(meth)acrylate, decanediol mono(meth)acrylate, nonanediol mono(meth)acrylate, octanediol mono(meth)acrylate, heptanediol mono(meth)acrylate, polyethylene glycol mono(meth)acrylates having more than four ethoxy units, polypropylene glycol mono(meth)acrylates having more than four propoxy units, pentaerythritol tri(meth)acrylate and di-pentaerythritol penta(meth)acrylate.

Preferred OH-functional (meth)acrylic acid derivatives of the formulae (IV) and (V) which may be mentioned are hexanediol mono(meth)acrylate, pentanediol mono(meth)acrylate, butanediol mono(meth)acrylate, tetraethylene glycol mono(meth)acrylate, tetrapropylene glycol mono(meth)acrylate and trimethylolpropane di(meth)acrylate.

Particularly preferred OH-functional (meth)acrylic acid derivatives are 3-hydroxypropyl (meth)acrylate, 2-hydroxyethyl (meth)acrylate, tri- and diethylene glycol mono(meth)acrylate, tri- and dipropylene glycol mono(meth)acrylate and glycerol di(meth)acrylate.

If isomers of the OH-functional (meth)acrylic acid derivatives of the formulae (III) and (IV) mentioned exist with respect to the position of the (meth)acryloyl group or with respect to the central hydrocarbon skeleton (branched or unbranched), the use of isomer mixtures is preferred.

The reaction of the diisocyanates and acid chlorides according to formula (II) to give the (meth)acrylic acid esters (I) according to the invention is preferably carried out in an inert solvent with the exclusion of water. Examples of suitable solvents are: chloroform, tetrahydrofuran, dioxane, methylene chloride, toluene, acetonitrile and Frigens. Preferred solvents are chloroform, tetrahydrofuran, Frigen 113, acetonitrile and methylene chloride.

The process according to the invention can in particular also be carried out in a low viscosity comonomer as the solvent, which itself contains (meth)acrylate groups and therefore does not have to be removed after the reaction, as it is copolymerizable with the compounds according to the invention. The monomer mixture obtained is thus directly suitable for the preparation of dental materials. Suitable reactive diluents are di(meth)acrylates of dihydric alcohols such as alkanediols or ethylene glycols and propylene glycols having two to twelve carbon atoms. Hexanediol dimethacrylate and triethylene glycol dimethacrylate are particularly suitable.

The reaction is in general carried out in the temperatures range from −40° to +100° C., preferably −35° to +70° C.

In order to accelerate the reaction of the diisocyanates according to formula (II), catalysts optionally containing tin such as dibutyltin dilaurate or tin(II) octoate are used. Other suitable catalysts are compounds containing tert. amino groups and titanium compounds. In general, the catalyst is employed in an amount of from 0.01 to 2.5 % by weight, preferably of from 0.1 to 1.5 % by weight, relative to the total amount of the reactants.

The reaction of the acid chlorides according to formula (II) can optionally be carried out in the presence of bases. Suitable bases are sodium hydroxide, potassium hydroxide, sodium carbonate or potassium carbonate, sodium hydrogen carbonate or potassium hydrogen carbonate and also tertiary amines such as triethylamine, pyridine, N-methylpiperidine, 1,5-diazabicyclo[4.3.0]non-5-ene or 1,8-diazabicyclo[5.4.0]undec-7-ene.

The process according to the invention is in general advantageously carried out under normal pressure in the presence of 0.01 to 0.2 % by weight of a polymerization inhibitor, relative to the total amount of the reactants. However, it is also possible to carry out the process according to the invention at a reduced or elevated pressure.

A suitable inhibitor is, for example, 2,6-di-tert.-butyl-p-cresol. Air is also suitable, and is passed into the reaction mixture. The process according to the invention can be carried out, for example, as follows:

The reactants are dissolved in the solvent and, if desired, the catalyst and/or the base are added with stirring. The progress of the reaction can be monitored, for example, by measurement of the IR spectra. After complete reaction of the isocyanate or acid chloride groups, the reaction products are isolated by removing the solvent after filtration of solids present. Prior purification with the aid of adsorbents, for example active carbon, bleaching earth, silica gel or alumina is possible.

For use as monomers for polymeric dental filling materials or coating agents (dental lacquers) in the dental field, the (meth)acrylic acid esters of the formula (I) according to the invention can be mixed with monomers known per se in order, for example, to adjust the viscosity to the intended use. Viscosities in the range from 60 to 20,000 mPa.s are preferred in this case. This can be achieved by optionally admixing a comonomer of lower viscosity to the monomers according to the invention. The compounds according to the invention are employed with a proportion of about 10 to 90 % by weight in the mixture with comonomers, a proportion of 20 to 80 % by weight being particularly preferred.

It is also possible to employ monomer mixtures which contain several comonomers.

The following comonomers may be mentioned as examples: triethylene glycol dimethacrylate, tetraethylene glycol dimethacrylate, 1,12-dodecanediol dimethacrylate, 1,6-hexanediol dimethacrylate, tri- and diethylene glycol dimethacrylate, bis-GMA, 2,2-bis[p-(2,-methacryloyloxyethoxy)phenyl]propane. Comonomers having urethane groups, for example the known reaction products of 1 mol of a diisocyanate, for example hexamethylene diisocyanate, trimethylhexamethylene diisocyanate or isophorone diisocyanate, with 2 mols of a hydroxyalkyl (meth)acrylate, for example glycerol dimethacrylate, 2-hydroxypropyl acrylate, etc., are also advantageous.

Other examples of comonomers are: trimethylolpropane tri(meth)-acrylate, bis-(meth)acryloyloxyethoxymeth-yl-tricyclo[5.2.1.0$^{2.6}$]decane (according to DE-A 2,931,925 and 2,931,926), 1,3-di[(meth)acryloyloxypropyl]-1,1,3,3-tetramethyl-disiloxane, 1,3-bis[3- (meth)acryloyloxyethylcarbamcyloxy-propyl]-1,1,3,3-tetramethyl-disiloxane. In particular, comonomers are preferred which have a boiling point above 100° C. at 13 mbar.

The (meth)acrylic acid esters (I) according to the invention can be used, if desired mixed with the monomers mentioned, for the preparation of polymeric materials. The polymerization yields polymers which have a high cross-linking density and a reduction in the polar components of the surface tension compared to conventional polymers. The (meth)acrylic acid derivatives (I) according to the invention can be used in particular as monomers for dental materials. Dental materials which may be mentioned, for example, are filling materials for teeth, coating agents for teeth and components for the production of dentures. Depending on the area of use, dental materials can contain other auxiliaries.

The (meth)acrylic acid esters (I) according to the invention can be cured, if desired mixed with the monomers mentioned, to give crosslinked polymers by methods known per se (G. M. Brauer, H. Argentar, Am. Chem. Soc., Symp. Ser. 212, pp. 359 to 371 [1983]). For the so-called redox polymerization, a system consisting of a peroxide compound and a reducing agent, for example based on tertiary aromatic amines, is suitable.

Examples of peroxides are: dibenzoyl peroxide, dilauroyl peroxide, di-4-chlorobenzene peroxide and dicyclohexyl peroxydicarbonate.

Examples of tertiary aromatic amines which may be mentioned are N,N-dimethyl-p-toluidine, bis-(2-hydroxyethyl)-p-toluidine, bis(2-hydroxyethyl)-3,5-dimethylaniline and N-methyl-N-(2-methylcarbamoyloxypropyl)-3,5-dimethylaniline described in DE-PS (German Patent Specification) 2,759,239.

The concentrations of the peroxide and the amine are advantageously selected so that they are 0.1 to 5% by weight, preferably 0.5 to 3% by weight, relative to the monomer mixture. The peroxide- or amine-containing monomer mixtures are stored separately until use.

The monomers according to the invention can also be made to polymerize by irradiation with UV light or visible light (for example in the wavelength region from 230 to 650 nm). Suitable initiators for the photo-initiated polymerization are, for example, benzil, benzil dimethyl ketal, benzoin monoalkyl ethers, benzophenone, p-methoxybenzophenone, fluorenone, thioxanthone, phenanthrenquinone and 2,3-bornanedione (camphorquinone), if desired in the presence of synergistically acting photoactivators, such as N,N-dimethylaminoethyl methacrylate, triethanolamine, 4-N,N-dimethylaminobenzenesulphonic acid bisallyl amide. The carrying out of the photopolymerization process is described, for example, in DE-PS (German Patent Specification) 3,135,115.

In addition to the initiators described above, light-screening agents and polymerization inhibitors known per se for this intended use can be added to the (meth)acrylic acid esters according to the invention. The light-screening agent and the polymerization inhibitor are in each case in general employed in an amount from 0.01 to 0.50 parts by weight, relative to 100 parts by weight of the monomer mixture. The monomer mixtures can be employed as coating agents for teeth (dental lacquers) without the addition of fillers. After the polymerization, a scratch-resistant coating is obtained on the substrate.

When used as dental filling materials, fillers are in general added to the monomer mixtures obtained. In order to be able to achieve a high degree of filling, monomer mixtures which have a viscosity in the range from 60 to 20,000 mPa.s are particularly advantageous. Inorganic fillers may preferably be admixed to the monomer mixtures containing the compounds of the formula (I) according to the invention. Examples which may be mentioned are glass ceramics containing rock crystal, quartzite, cristobalite, quartz glass, highly disperse silicic acid, alumina and glass ceramics, for example lanthanum and zirconium (DE-A 2,347,591).

The inorganic fillers are preferably pretreated with an adhesion promoter to improve the bonding to the polymer matrix of the polymethacrylate. The adhesion promotion can be achieved, for example, by treatment with organosilicon compounds [E. P. Plueddemann, Progress in Organic Coatings, 11, 297 to 308 (1983)]. 3-Methacryloyloxypropyltrimethoxysilane is preferably employed.

The fillers for the dental filling materials according to the invention in general have an average particle diameter of 0.01 to 100 μm, preferably of 0.05 to 50 μm, particularly preferably 0.05 to 5 μm. It may also be advantageous to employ several fillers which have a different particle diameter and different degree of silanization from one another together.

The proportion of the filler in the dental filling materials is in general 5 to 85% by weight, preferably 50 to 80% by weight.

For the preparation of the dental filling materials, the components are processed using commercial kneading machines.

The proportion of (meth)acrylic acid derivatives according to the invention in the filling materials is in general 5 to 90% by weight, preferably 10 to 60% by weight, relative to the filling material. The curing of the dental filling materials to give a shaped article is carried out in the cavity of the tooth using the above-mentioned methods.

The (meth)acrylic acid derivatives according to the invention can also be employed as components in the production of dentures.

In this case, the monomers according to the invention are combined with the customarily used constituents which are known per se. Preferably, the monomers are employed in a mixture with alkyl methacrylates, such as methyl methacrylate Bead polymers known per se may also additionally be added. In order to adjust the color of the teeth, known inorganic and organic color pigments and opacifiers can be added. The use of stabilizers and light-screening agents is also possible.

The artificial teeth are produced by free radical polymerization of the dental materials under molding conditions. Processing is possible both by injection processes and stamping processes and is in general carried out by the customary production methods for teeth based on poly(methyl methacrylates), for example by thermal polymerization using polymerization initiators known per se, for example based on peroxides and azo compounds, such as dibenzoyl peroxide, dilauroyl peroxide, cyclohexyl percarbonate and azoisobutyrodinitrile. Mixtures of polymerization initiators having differing half lives with respect to their decomposition are also highly suitable.

EXAMPLES

EXAMPLE 1

Reaction of 1,2-bis-(4,-isocyanatophenoxy)-3,3,4,4,5,5-hexafluoro-1-cyclopentene (A) with glycerol dimethacrylate (GDMA)

91.75 g (0.402 mol) of GDMA were added dropwise with stirring to a solution of 88.90 g (0.201 mol) of isocyanate A in 170 g of dry chloroform, the temperature rising to 61° C. The mixture was stirred at room temperature for a further eleven hours, 0.60 g each of 2,6-di-tert.butyl-p-cresol and hydroquinone monomethyl ether were added and the mixture was concentrated to give 178.24 g (98% of theory) of a pale, viscous oil of the product "A-GDMA$_2$" (see above).

IR (Film): $\nu$=3300, 2900, 1720, 1632, 1608, 1522, 1500, 1351, 1283, 1185, 1150, 1000, 973, 940, 754 cm$^{-1}$.

$^1$H-NMR (CDCl$_3$, 200 MHz): $\delta$=1.97 (bs, 12 H, CH$_3$), 4.30 (m, 10 H, CH$_2$—CH—CH$_2$), 5.62, 6.15 (2 m, each 4 H, vinyl. H), 6.71, 7.20 (2 m, each 4 H, ar. H), 6.95 (bs, 2 H, NH) ppm.

HPLC/MS (NH$_3$ activation): m/e=898 (M$^+$), 670 (M-GDMA)

MS (70 eV direct inlet):

m/e = 584 (M-GDMA-⋀CO$_2$H),

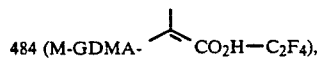

484 (M-GDMA-⋀CO$_2$H—C$_2$F$_4$),

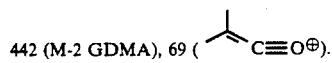

442 (M-2 GDMA), 69 (⋀C≡O$^⊕$).

EXAMPLE 2

Reaction of 1,2-bis-(4,-isocyanatophenoxy)-3,3,4,4,5,5-hexafluoro-1-cyclopentene (A) with 2-hydroxyethyl methacrylate (HEMA)

117.65 g (904 mmol) of HEMA were added dropwise at room temperature with stirring to a solution of 200.00 g (452 mmol) of isocyanate A in 375.00 g of dry chloroform and the mixture was heated to 50° C. for five hours. After adding 1.71 g each of 2,6-di-tert.butyl-p-cresol and hydroquinone monomethyl ether, the mixture was concentrated to give 316.76 g (99% of theory) of a pale oil of the product "A-HEMA$_2$" (see above).

IR (Film): $\nu$=3280, 2900, 1701, 1620, 1600, 1520, 1500, 1360, 1280, 1208, 1180, 1151, 1067, 992, 963 cm$^{-1}$.

$^1$H-NMR (CDCl$_3$, 200 MHz): $\delta$=1.97 (bs, 6 H, CH$_3$), 4.42 (bs, 8 H, CH$_2$), 5.61, 6.17 (2 m, each 2 H, vinyl. H), 6.67, 7.16 (2 m, each 4 H, ar. H), 6.71 (bs, 2 H, NH) ppm.

MS (70 eV): m/e=702 (M$^+$), 572 (M-HEMA), 442 (M-2HEMA),

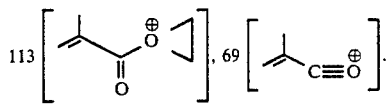

EXAMPLE 3

Reaction of 1,2-bis-[4,-(chlorocarbonyl)phenoxy]-3,3,4,4,5,5-hexafluoro-1-cyclopentene (B) with 2-hydroxyethyl methacrylate (HEMA)

65.20 g (500 mmol) of HEMA, 60.80 g (600 mmol) of dry triethylamine and 50 mg of 2,6-di-tert.butyl-cresol were initially introduced together into 250 ml of dry methylene chloride and a solution of 121.30 g (250 mmol) of acid chloride B in 200 ml of methylene chloride was added at -30° C. The mixture was stirred at −30° C. for two hours, the precipitate deposited was filtered off with suction at 0° C. and the filtrate obtained was extracted with water. 50 mg of hydroquinone monomethyl ether were added to the dried organic phase and the mixture was concentrated to give 157.20 g (93% of theory) of a pale oil of the product "B-HEMA$_2$" (see above).

IR (Film): $\nu$=2940, 1720, 1618, 1602, 1500, 1445, 1270, 1150, 1002, 978, 940, 845, 809, 760 cm$^{-1}$.

$^1$H-NMR (CDCl$_3$, 200 MHz): $\delta$=1.96 (bs, 6 H, CH:), 4.50 (m, 8 H, CH$_2$), 5.61, 6.13 (2 m, each 2 H, vinyl. H), 6.78, 7.82 (2 m, each 4 H, ar. H) ppm.

EXAMPLE 4

Reaction of 1,2-bis-[4,-(chlorocarbonyl)phenoxy]-3,3,4,4,5,5-hexafluoro-1-cyclopentene (B) with glycerol dimethacrylate (GDMA)

114.00 g (500 mmol) of glycerol dimethacrylate, 60.80 g (600 mmol) of dry triethylamine and 50 mg of 2,6-di-tert.butyl-p-cresol were initially introduced together into 250 ml of dry methylene chloride and a solution of 121.30 g (250 mmol) of acid chloride B in 250 ml of methylene chloride was added at −30° C. The procedure was then as in Example 3 and 205.56 g (94% of theory) of a pale oil of the product "B-GDMA$_2$" (see above) were obtained.

IR (Film): $\nu$2960, 1730, 1640, 1605, 1500, 1350, 1321, 1295, 1267, 1205, 1157, 1110, 1005, 979, 942, 847, 810, 759, 730 cm$^{-1}$.

$^1$H-NMR (CDCl$_3$, 200 MHz): $\delta$=1.93 (bs, 12 H, CH:), 4.40 (m, 10 H, CH$_2$—CH—CH$_2$), 5.61, 6.11 (2 m, each 4 H, vinyl. H), 6.77, 7.86 (2 m, each 4 H, ar. H) ppm.

EXAMPLE 5

Reaction of 1,2-bis-[4,-(isocyanato-2,-trifluoromethyl-phenoxy)-3,3,4,4,5,5-hexafluoro-1-cyclopentene (C) with 2-hydroxypropyl methacrylate (HPMA) and glycerol dimethacrylate (GDMA)

A solution of 14.42 g (100 mmol) of HPMA and 22.82 g (100 mmol) of GDMA in 10 ml of dry chloroform was added dropwise at room temperature with stirring to a solution of 57.83 g (100 mmol) of isocyanate C in 120 ml of dry chloroform. The mixture was heated to 40° C. for four hours and then concentrated to give 91.10 g (96% of theory) of a yellowish oil which consisted of the three reaction products "C-GDMA-HPMA", "C-HPMA$_2$" and "C-GDMA$_2$" (see above).

IR (Film). $\nu$=3300, 2940, 1710, 1620, 1540, 1492, 1420, 1320, 1200, 1130, 1044, 1000, 973, 940, 752 cm$^{-1}$.

$^1$H-NMR (CDCl$_3$, 200 MHz): δ=1.3 (OCH—CH$_3$), 1.98 (=CCH$_3$), 3.6–4.6 (OCH$_2$, OCH), 5.6, 6.15 (=CH$_2$), 6.8–7.7 (ar.-H, NH) ppm.

EXAMPLE 6

0.2% by weight of camphorquinone and 0.5% by weight of 4-N,N-dimethylaminobenzene sulphonic acid bisallylamide are added to 3 parts of the (meth)acrylic acid ester, according to the invention, of Example 1 and 1 part of triethylene glycol dimethacrylate and the mixture is processed with the exclusion of light to give an activated monomer mixture(0). This is cured by visible light during a period of exposure of 60 s to give a plastic of high mechanical stability and can be used as a sealing material in the dental field (sealer, liner, dental lacquer).

In order to prepare a dental filling material, 29 parts by weight of the activated not polymerized monomer mixture (D) and 71 parts by weight of a mixture of pyrogenic silicic acid and ground quartz glass silanized using 3-methacryloyloxypropyltrimethoxysilane are processed to give a paste at room temperature in a commercially available kneader. A sample, cured according to DIN 13 922 using a commercially available dental lamp (Translux ®), which was prepared from this paste also showed a good resistance to abrasion in addition to a high flexural strength and low water absorption.

It will be understood that the specification and examples are illustrative but not limitative of the present invention and that other embodiments within the spirit and scope of the invention will suggest themselves to those skilled in the art.

We claim:

1. A (xeth)acrylic acid ester of a substituted 1,2-bis-(phenoxy)-3,3,4,4,5,5-hexafluoro-1-cyclopentenes of the formula

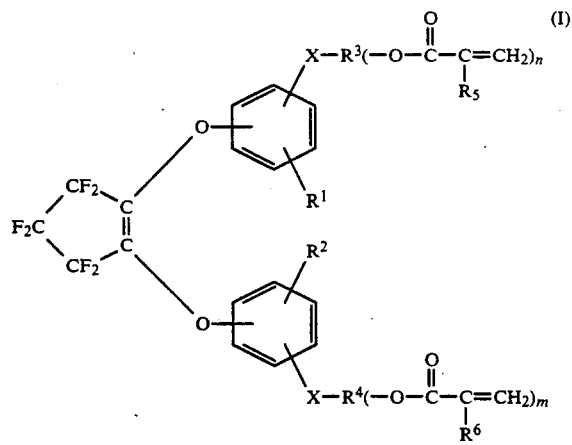

in which, in each case independently of one another,
R$^1$ and R$^2$ denote C$_1$- to C$_4$-alkyl, C$_1$- to C$_4$-halogenoalkyl or hydrogen,
R$^3$ and R$^4$ denote (n+1)- or (m+1)-valent, straight-chain or branched hydrocarbon radicals having 2 to 15 carbon atoms, which may optionally contain 1 to 3 oxygen bridges,
R$^5$ and R$^6$ denote hydrogen or methyl,
X represents

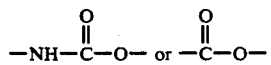

and
n and m denote integers from 1 to 5.

2. A (meth)acrylic acid ester of a substituted 1,2-bis-(phenoxy)-3,3,4,4,5,5-hexafluoro-1-cyclopentenes according to claim 1, where, in each case independently of one another,
R$^1$ and R$^2$ denote hydrogen or trifluoromethyl,
R$^3$ and R$^4$ denote (n+1)- or (m+1)-valent, straight-chain or branched hydrocarbon radicals having 2 to 15 carbon atoms,
R$^5$ and R$^6$ denote hydrogen or methyl and
X represents

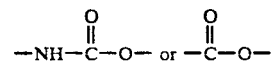

and
n and m denote 1 or 2.

3. A process for the preparation of a (meth)acrylic acid ester according to claim 1, comprising reacting a substituted 1,2-bis(phenoxy)-3,3,4,4,5,5-hexafluoro-1-cyclopentene of the formula

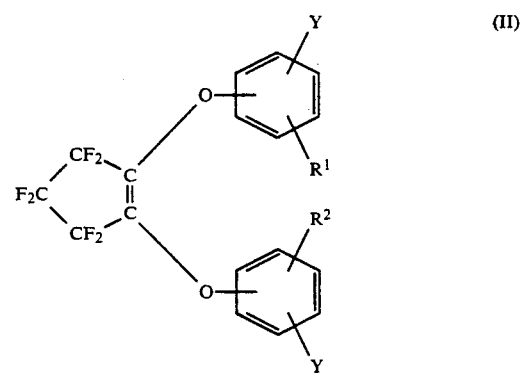

in which
Y represents isocyanato (—NCO) or chlorocarbonyl (—COCl),
with at least one OH-functional (meth)acrylic acid derivative of the formula

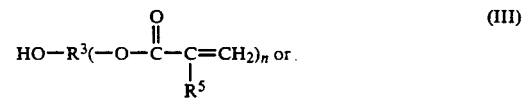

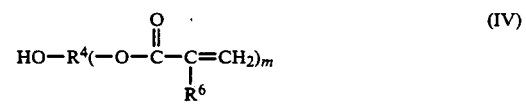

in an inert solvent at a temperature between −40° and +100° C., optionally in the presence of a catalyst, base or polymerization inhibitor.

4. A polymer prepared from a monomer according to claim 1.

5. A dental filling material comprising a polymer according to claim 4, and a filler.

6. An artificial tooth comprising a polymer according to claim 4.

7. In the filling of a tooth with a composition including a polymerizable monomer, the improvement wherein such monomer comprises an acrylic or methacrylic acid ester of a substituted 1,2-bis-(phenoxy)-

3,3,4,4,5,5-hexafluoro-1-cyclopentene according to claim 1.

8. In the coating of a tooth with a composition including a polmerizable monomer, the improvement wherein such monomer comprises an acrylic or methacrylic acid ester of a substituted 1,2,-bis-(phenoxy)-3,3,4,4,5,5-hexafluoro-1-cyclopentene according to claim 1.

9. In the preparation of an artificial tooth by polymerizing in a form a composition including a polymerizable monomer, the improvement wherein such monomer comprises an acrylic or methacrylic acid ester of a substituted 1,2-bis-(phenoxy)-3,3,4,4,5,5-hexafluoro-1-cyclopentene according to claim 1.

* * * * *

UNITED STATES PATENT AND TRADEMARK OFFICE
CERTIFICATE OF CORRECTION

PATENT NO. : 5,132,335

DATED : July 21, 1992

INVENTOR(S) : Muller et al.

It is certified that error appears in the above-identified patent and that said Letters Patent is hereby corrected as shown below:

Col. 17, line 33   Delete " xeth " and substitute -- meth --

Signed and Sealed this

First Day of March, 1994

Attest:

BRUCE LEHMAN

Attesting Officer         Commissioner of Patents and Trademarks